United States Patent [19]
Gref et al.

[11] Patent Number: 5,565,215
[45] Date of Patent: Oct. 15, 1996

[54] BIODEGRADABLE INJECTABLE PARTICLES FOR IMAGING

[75] Inventors: Ruxandra Gref, Nancy, France; Yoshiharu Minamitake, Brookline; Robert S. Langer, Newton, both of Mass.

[73] Assignee: Massachusettes Institute of Technology, Cambridge, Mass.

[21] Appl. No.: 210,677

[22] Filed: Mar. 18, 1994

Related U.S. Application Data

[63] Continuation-in-part of Ser. No. 96,370, Jul. 23, 1993.

[51] Int. Cl.$^6$ .............................. A61K 9/50; A61K 9/48; A61K 31/74; A61K 47/30
[52] U.S. Cl. .............. 424/501; 424/489; 424/497; 424/498; 424/502; 424/451; 424/462; 424/78.08; 514/772.3; 514/784; 514/963; 428/402.21; 428/402.24; 428/403
[58] Field of Search ........................... 424/78.08, 451, 424/462, 489, 497, 498, 501, 502; 514/963, 772.3, 784; 428/402.21, 402.24, 403

[56] References Cited

U.S. PATENT DOCUMENTS

| | | | |
|---|---|---|---|
| 4,801,739 | 1/1989 | Franz et al. | 560/185 |
| 4,904,479 | 2/1990 | Illum | 242/490 |

FOREIGN PATENT DOCUMENTS

| | | |
|---|---|---|
| 0092918 | 11/1983 | European Pat. Off. . |
| 0166596 | 1/1986 | European Pat. Off. . |
| 0295055 | 12/1988 | European Pat. Off. . |
| 0552802 | 7/1993 | European Pat. Off. . |
| WO94/02122 | 2/1994 | United Kingdom . |

OTHER PUBLICATIONS

Brich, Z. et al., "Branched Ter–Polyesters: Synthesis, Characterization, In Vitro and In Vivo Degradation Behaviour", *Proceed. Intern. Symp. Control. Rel. Bioact. Mater.* 15:95–96 (1988).

Jedlinski, Zbigniew, et al., "Synthesis of ethylene glycol–L–lactide block copolymers," *Makromol. Chem.* 194: 1681–1689 (1993).

Primary Examiner—Carlos Azpuru
Attorney, Agent, or Firm—Arnall Golden & Gregory

[57] ABSTRACT

Injectable nanoparticles or microparticles are provided that are not rapidly cleared from the blood stream by the macrophages of the reticuloendothelial system, and that can be modified as necessary to achieve variable release rates or to target specific cells or organs as desired. The terminal hydroxyl group of the poly(alkylene glycol) can be used to covalently attach onto the surface of the injectable particles biologically active molecules, including antibodies targeted to specific cells or organs, or molecules affecting the charge, lipophilicity or hydrophilicity of the particle. The surface of the particle can also be modified by attaching biodegradable polymers of the same structure as those forming the core of the injectable particles. The injectable particles include magnetic particles or radioopaque materials for diagnostic imaging.

30 Claims, 4 Drawing Sheets

FIG. 8

BIODEGRADABLE INJECTABLE PARTICLES FOR IMAGING

This is a continuation in part of U.S. Ser. No. 08/096,370 entitled "Biodegradable Injectable Nanoparticles" filed Jul. 23, 1993 by Ruxandra Gref, Yoshiharu Minamitake, and Robert S. Langer.

This invention is in the area of biodegradable and injectable nanoparticles and microparticles for the controlled delivery of biologically active materials and diagnostic agents.

BACKGROUND OF THE INVENTION

A major challenge in the area of the parenteral administration of biologically active materials is the development of a controlled delivery device that is small enough for intravenous application and which has a long circulating half-life. Biologically active materials administered in such a controlled fashion into tissue or blood are expected to exhibit decreased toxic side effects compared to when the materials are injected in the form of a solution, and may reduce degradation of sensitive compounds in the plasma.

A number of injectable drug delivery systems have been investigated, including microcapsules, microparticles, liposomes and emulsions. A significant obstacle to the use of these injectable drug delivery materials is the rapid clearance of the materials from the blood stream by the macrophages of the reticuloendothelial system (RES). For example, polystyrene particles as small as sixty nanometers in diameter are cleared from the blood within two to three minutes. By coating these particles with block copolymers based on poly(ethylene glycol) and poly(propylene glycol), their half-lives were significantly increased. L. Illum, S. S. Davis, "The organ uptake of intravenously administered colloidal particles can be altered by using a non-ionic surfactant (poloxamer 338)", *FEBS Lett.*, 167, 79 (1984). Polystyrene particles, however, are not biodegradable and therefore not therapeutically useful.

Liposomal drug delivery systems have been extensively considered for the intravenous administration of biologically active materials, because they were expected to freely circulate in the blood. It was found, however, that liposomes are quickly cleared from the blood by uptake through the reticuloendothelial system. The coating of liposomes with poly(ethylene glycol) increases their half life substantially. The flexible and relatively hydrophilic PEG chains apparently induce a stearic effect at the surface of the liposome that reduces protein adsorption and thus RES uptake. T. M. Allen, C. Hansen, *Biochimica et Biophysica Acta*, 1068, 133–141 (1991); T. M. Allen, et al., *Biochimica et Biophysica Acta*, 1066, 29–36 (1991); V. Torchilin, A. Klibanov, "The antibody-linked Chelating Polymers for Nuclear Therapy and Diagnostics", *Critical Reviews in Therapeutic Drug Carrier Systems*, 7(4), 275–307 (1991); K. Maruyama, et al., *Chem. Pharm. Bull.*, 39(6), 1620–1622 (1991); M. C. Woodle, et al., *Biochimica et Biophysica Acta;* 193–200 (1992); and D. D. Lassic, et al., *Biochimica et Biophysica Acta*, 1070, 187–192 (1991); and A. Klibanov, et al., *Biochimica et Biophysica Acta*, 1062, 142–148 (1991).

European Patent Application Nos. 0 520 888 A1 and 0 520 889 A1 disclose nanoparticles of the block copolymer of polylactic acid and poly(ethylene glycol) for the injectable controlled administration of biologically active materials. The applications do not disclose how to modify the copolymer to vary the profile of drug release nor how modification of the copolymer would affect distribution and clearance of the delivery devices in vivo. The applications also do not teach how to prepare nanoparticles that are targeted to specific cells or organs, or how to prepare nanospheres that are useful for gamma-imaging for diagnostic purposes.

U.S. Pat. No. 5,145,684 discloses stable, dispersible drug nanoparticles prepared by wet milling in the presence of grinding media in conjunction with a surface modifier.

It would be desirable to have injectable particles for the controlled delivery of biologically active materials that are not rapidly cleared from the blood stream by the macrophages of the reticuloendothelial system, and that can be modified as necessary to target specific cells or organs or manipulate the rate of delivery of the material.

Therefore, it is an object of the present invention to provide injectable particles for the controlled delivery of biologically active materials that are not rapidly cleared from the blood stream.

It is another object of the present invention to provide injectable particles that can be modified as necessary to target specific cells or organs or manipulate the rate of delivery of the material.

It is another object of the present invention to provide injectable biodegradable particles that contain magnetic materials for diagnostic imaging.

It is still another object of the present invention to provide microparticles for the controlled release of substances or for diagnostic imaging that can optionally be targeted to specific organs or cells.

SUMMARY OF THE INVENTION

Injectable particles are provided that are not rapidly cleared from the blood stream by the macrophages of the reticuloendothelial system, and that can be modified as necessary to achieve variable release rates or to target specific cells or organs as desired. The particles have a biodegradable solid core containing a biologically active material and/or contrast agent for imaging and poly(alkylene glycol) moieties on the surface. The terminal hydroxyl group of the poly(alkylene glycol) can be used to covalently attach onto the surface of the injectable particles biologically active molecules, including antibodies targeted to specific cells or organs, or molecules affecting the charge, lipophilicity or hydrophilicity of the particle. The surface of the particle can also be modified by attaching biodegradable polymers of the same structure as those forming the core of the injectable particles. The typical size of the particles is between 1 nm and 1000 nm, preferably between 1 nm and 100 nm, although microparticles having larger diameters can also be formed as described herein.

The injectable particles can include magnetic particles or radioopaque materials for diagnostic imaging, biologically active molecules to be delivered to a site, or compounds for targeting the particles.

The injectable particles are useful to administer biologically active materials in a controlled manner intravenously for a wide variety of purposes. The injectable particles can be fabricated in a one-step procedure, and are easily lyophilized and redispersed in aqueous solutions. Biodistribution experiments indicate that the injectable particles have a prolonged half-life in the blood compared to particles not containing poly(alkylene glycol) moieties on the surface.

DETAILED DESCRIPTION OF THE INVENTION

Injectable particles are disclosed that are not rapidly cleared from the blood stream by the macrophages of the reticuloendothelial system, and that can be modified as necessary to achieve variable release rates or to target specific cells or organs as desired. The particles are useful to administer biologically active materials in a controlled manner for a wide variety of purposes.

Size of Particles

As described herein, the typical size of the injectable particles is between 1 nm and 1000 nm, preferably between 1 nm and 100 nm. Although the methodology produces particles between 1 and 1000 nm, or nanoparticles, it is possible to increase the diameter of the resulting particles to for microparticles having a diameter of 1 micron or greater. For ease of reference herein in the general descriptions, both microparticles and nanoparticles will be referred to as injectable particles unless otherwise specified.

As used herein, the term nanoparticle refers to a solid particle of size ranging from 10 to 1000 nm. The 'ideal' nanoparticle is biodegradable, biocompatible, has a size of less than 200 nm and has a rigid biodegradable core that has incorporated in it the substance to be delivered.

The term "microparticle," as used herein, refers to a particle of size ranging from greater than one micron to 1000 microns. Any of the nanoparticles described herein can be alternatively fabricated as microparticles if more appropriate for the desired application.

Structure of Particles

Figure 1:
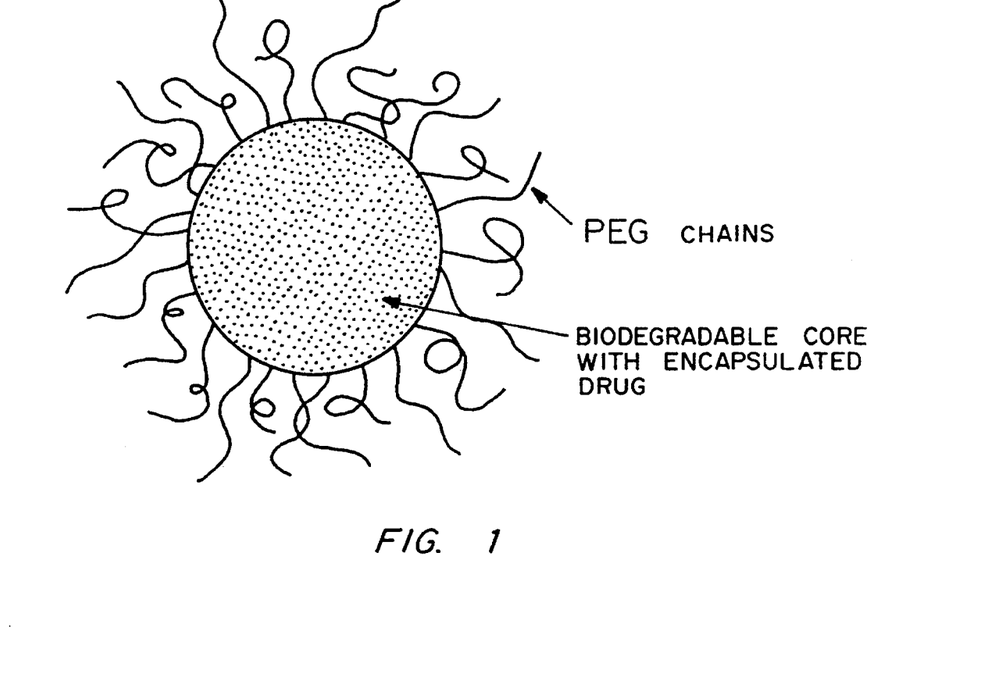
FIG. 1 is a schematic representation of a cross-section of a nanosphere prepared as described herein that has a biodegradable solid core containing a biologically active material and poly(ethylene glycol) moieties on the surface.

FIG. 1 is a schematic representation of a cross-section of a nanoparticle prepared as described herein. As illustrated, the particle has a biodegradable solid core containing a biologically active material and poly(alkylene glycol) moieties on the surface. The surface poly(alkylene glycol) moieties have a high affinity for water that reduces protein adsorption onto the surface of the particle. The recognition and uptake of the nanoparticle by the reticulo-endothelial system (RES) is therefore reduced. The terminal hydroxyl group of the poly(alkylene glycol) can be used to covalently attach biologically active molecules, or molecules affecting the charge, lipophilicity or hydrophilicity of the particle, onto the surface of the nanoparticle.

A nanosphere refers to a nanoparticle that is spherical in shape. The shape of the nanoparticles prepared according to the procedures herein or otherwise known is easily determined by scanning electron microscopy. Spherically shaped nanoparticles are preferred for circulation through the bloodstream. If desired, the particles can be fabricated using known techniques into other shapes that are more useful for a specific application.

Degradation Properties

The term biodegradable or bioerodible, as used herein, refers to a polymer that dissolves or degrades within a period that is acceptable in the desired application (usually in vivo therapy), usually less than five years, and preferably less than one year, on exposure to a physiological solution of pH 6–8 having a temperature of between $25°$ and $37°$ C. In a preferred embodiment, the nanoparticle degrades in a period of between 1 hour and several weeks, according to the application.

Composition of Particles

There are a number of specific embodiments of the injectable particles described herein. In a first embodiment, an injectable particle is provided that includes a substance to be delivered and a diblock, triblock, or multiblock copolymer of poly(alkylene glycol) with poly(lactic-co-glycolic acid). In a second embodiment, an injectable particle is provided that includes a substance to be delivered and a copolymer of poly(alkylene glycol) with a polyanhydride, polyhydroxybutyric acid, polyorthoesters other than the homopolymer of lactic acid, polysiloxanes, polycaprolactone, or copolymers prepared from the monomers of these polymers, wherein the copolymer can be of diblock, triblock, or multiblock structure. Alternatively, the injectable particle can include a substance to be delivered and a copolymer of the form poly(alkylene glycol)-[poly(lactic-co-glycolic acid) or poly(lactic acid)]-poly(alkylene glycol). In yet another embodiment, the injectable particle includes a substance to be delivered and a copolymer of a poly(lactic acid) or poly(glycolic acid), with two or more moieties of poly(alkylene glycol). Alternatively, the injectable particle can include a substance to be delivered and a copolymer of a poly(lactic-co-glycolic acid), poly(lactic acid), or poly(glycolic acid) with poly(alkylene glycol), wherein the copolymer is blended with poly(lactic-co-glycolic acid).

Modification of Surface Properties of Particles

Alternatively, the poly(alkylene glycol) can be bound to a compound that affects the charge or lipophilicity or hydrophilicity of the particle.

For example, a polymer other than poly(alklene glycol) is used as the surface hydrophilic coating. Any biocompatible hydrophilic polymer can be used for this purpose, including but not limited to poly(vinyl alcohol). The particle can also be coated with a dextran, which are in general more hydrophilic than poly(alkelene glycol) but less flexible. Dextran coated nanoparticles are useful for magnetic resonance imaging (MRI).

Incorporation of Molecules for Targeting

Molecules can be bound to the particles to target them to a particular site in the body. For example, in one embodiment, an injectable particle is provided that includes a targeting molecule, for example, an antibody or antibody fragment, such as Fab or $Fab_2$ antibody fragments, covalently bound to the exterior of the particle. Examples of other useful targeting molecules include homones, sugars, and other compounds specifically bound to particular receptors or cell types.

Incorporation of Materials into the Particles

Biologically active materials can also be incorporated into the particles, as can contrast agents for imaging purposes. In the preferred embodiment, more than 30% by total weight, more preferably greater than 45%, of material is encapsulated in the particle, with an efficiency of at least 80%, more preferably greater than 90%. The biologically active molecule can be a protein, carbohydrate or polysaccharide, nucleic acid, lipid, a combination thereof, or a synthetic molecule, including organic and inorganic materials. Any of the drugs that are routinely adminstered by intravenous, or transdermal adminstration can be incorporated for delivery and controlled and/or prolonged release using the particles described herein.

In a preferred embodiment, the injectable particle includes a substance to be delivered and a copolymer of poly(alkylene glycol) with poly(lactic-co-glycolic acid), poly(lactic-acid), poly(glycolic acid), or polyanhydride, wherein the poly(alkylene glycol) is covalently bound to an antibody or antibody fragment.

The injectable particles can be used to release over long periods of time highly active and effective drugs, such as anticancer drugs, that produce significant side effects when administered systemically. The controlled release generally decreases the toxic side effects associated with systemic administration of the non-encapsulated drug. The polymeric matrix can also provide protection of the drugs against degradation in the plasma for drugs with short biological half-lives.

Incorporation of Substances for Diagnostic Purposes

Contrast agents that can be incorporated include gases, which are particular useful in ultrasound imaging. Any desired inert gas can be incorporated into the polymeric materials at the time of hydrogel formation, including air, argon, nitrogen, carbon dioxide, nitrogen dioxide, methane, helium, neon, oxygen and perfluorocarbon. Sterilized air or oxygen is a preferred imaging contrast agent.

Examples of suitable materials for MRI include the gatalinium chelates currently available, such as diethylene triamine pentacetic acid (DTPA) and Gatopentotate dimeglumine, as well as iron, magnesium, manganese, copper and chromium. These are typically administered in a dosage equivalent to 14 ml for a 70 kg person of a 0.5 M/liter solution.

Examples of materials useful for CT and x-rays include iodine based materials for intravenous administration such as ionic monomers typified by Diatrizoate and iothalamate (administered at a dosage of 2.2 ml of a 30 mg/ml solution), non-ionic monomers typified by iopamidol, isohexol, and ioversol (administered at a dosage of 2.2 ml 150–300 mg/ml), non-ionic dimers typified by iotrol and iodixanol, and ionic dimers, for example, ioxagalte. Other useful materials include barium for oral use.

In another embodiment, a gamma-labelled injectable nanoparticle is provided that can be used to monitor the biodistribution of the injectable particle in vivo. Any pharmaceutically acceptable gamma-emitting moiety can be used, including but not limited to indium and technectium. The magnetic particles can be prepared as described herein, or alternatively, magnetic nanoparticles, including surface-modified magnetic nanoparticles can be purchased commercially, the surface further modified by attaching the hydrophilic polymeric coating. For example, the magnetic nanoparticle can be mixed with a solution of the hydrophilic polymer in a manner that allows the covalent binding of the hydrophilic polymer to the nanoparticle. Alternatively, a gamma-emitting magnetic moiety is covalently attached to the hydrophilic or hydrophobic polymeric material of the particle.

Other materials can also be incorporated into the injectable particles for diagnostic purposes, including fluorescent compounds. Hydrophobic fluorescent compounds such as rhodamine can be incorporated into the core of the injectable particles. Hydrophilic fluorescent compounds can also be incorporated, however, the efficiency of encapsulation is smaller, because of the decreased compatibility of the hydrophobic core with the hydrophilic material. The hydrophilic material must be dissolved separately in water and a multiple emulsion technique used for fabrication of the particle.

The larger the size of the magnetic moiety, the larger the size of the resulting particles obtained using PLGA-PEG, or blends of PLGA-PEG with another polymer.

1. Detection of Gas Microbubbles

Due to their in vivo stability, the particles are useful for vascular imaging in liver and renal diseases, fallopian tube diseases, detecting and characterizing tumor masses and tissues, and measuring peripheral blood velocity, as well as the more standard applications.

The method for imaging by detection of gas bubbles in the particles in a patient uses a transducer which produces pulses, illustrative of ultrasonic acoustic energy, having predetermined frequency characteristics. A first pulse has an increasing frequency with time, and a second pulse has a decreasing frequency with time. Imaging arrangements produce images of the region within the specimen after exposure to the first and second pulses.

The conventional technique for determining the presence of bubbles in the blood stream uses a Doppler shift in the frequency of the ultrasonic acoustic energy which is reflected by the blood. The amplitude of the Doppler bubble signal increases nearly proportionally with increases in the radius of the bubble. The human hearing mechanism is considered the most accurate processor for recognizing whether bubble signals are present or absent. For this reason, it is preferable to have a skilled operator to obtain satisfactory results using Doppler blood flow monitoring equipment.

To determine whether the air-filled particles are useful for in vivo imaging, the following in vitro method can be used.

Particles prepared by the above methods are suspended in a capped tissue culture tube. For ultrasound imaging, the tubes are placed on top of a pad covered with coupling medium above the transducer. The transducer is held in place at roughly a 90° angle of incidence to minimize any motion artifacts. The transducer acts as a transmitter and also receives ultrasound radiation scattered back from the tube. B-mode and Doppler images are established for tubes filled with polymeric microcapsules and the resulting images are compared with a control consisting of an image from a tube containing buffer alone. The B-mode of display gives a two dimensional image of a slice through the scanned tube. The results correlate well with the in vivo results, as shown by Doppler imaging techniques (described below). Since the in vitro and in vivo data showed a high degree of correlation in the working examples, this test is reasonably predictive of the in vivo stability of microparticles.

2. Detection of Other Contrast Agents

Other means of detection include PET (positron emission tomograph), (CAT) computer assisted tomography, x-rays, fluoroscopy, and MRI (magnetic resonance imaging). These are conducted using the standard techniques and equipment as used with other commercialy available contrast agents.

The same particles useful in imaging using the more common techniques such as ultrasound, magnetic resonance imaging (MRI), computer tomography (CT), x-ray, are useful in the the less common positron emission tomography (PET) and single photon emission computerized tomography (PET).

Attachment of Specific Ligands to Particle Surfaces

The injectable particles prepared as described herein can be used for cell separation, as well as targeted to specific tissues, by attaching to the surface of the particle specific ligands for given cells in a mixture of cells. When magnetic particles are also incorporated, the particles can be targeted using the ligands, such as tissue specific receptors or antibodies to tissue specific surface proteins, then maintained at the targeted cells using a magnetic field while the particles are imaged or a compound to be delivered is released.

For example, in one embodiment, carmustine (BCNU) or other anti-cancer agent such as platon is incorporated in the core of the injectable particles and antibodies to the target cancerous cells are covalently bound to the surface of the injectable particle.

The materials that can be used to construct the injectable particles and methods for the preparation and use of the injectable particles are described in detail below. Given this description, one of skill in the art will be able to produce a wide variety of injectable particles for a range of applications, all of which are intended to fall within the scope of this invention.

I. Copolymers for the Construction of Injectable Nanospheres

The period of time of release, and kinetics of release, of the substance from the nanoparticle will vary depending on the copolymer or copolymer mixture or blend selected to fabricate the nanoparticle. Given the disclosure herein, those of ordinary skill in this art will be able to select the appropriate polymer or combination of polymers to achieve a desired effect.

Selection of Polymers

Poly(alkylene glycol) (which can also be referred to as a poly(alkylene oxide), if the polymer was prepared from an oxide instead of a glycol) is employed as the terminal hydrophilic block or blocks of the block copolymer. As used herein, the term poly(alkylene glycol) refers to a polymer of the formula HO—[(alkyl)O]$_y$—OH, wherein alkyl refers to a $C_1$ to $C_4$ straight or branched chain alkyl moiety, including but not limited to methyl, ethyl, propyl, isopropyl, butyl, and isobutyl. Y is an integer greater than 4, and typically between 8 and 500, and more preferably between 40 and 500.

Figure 7:
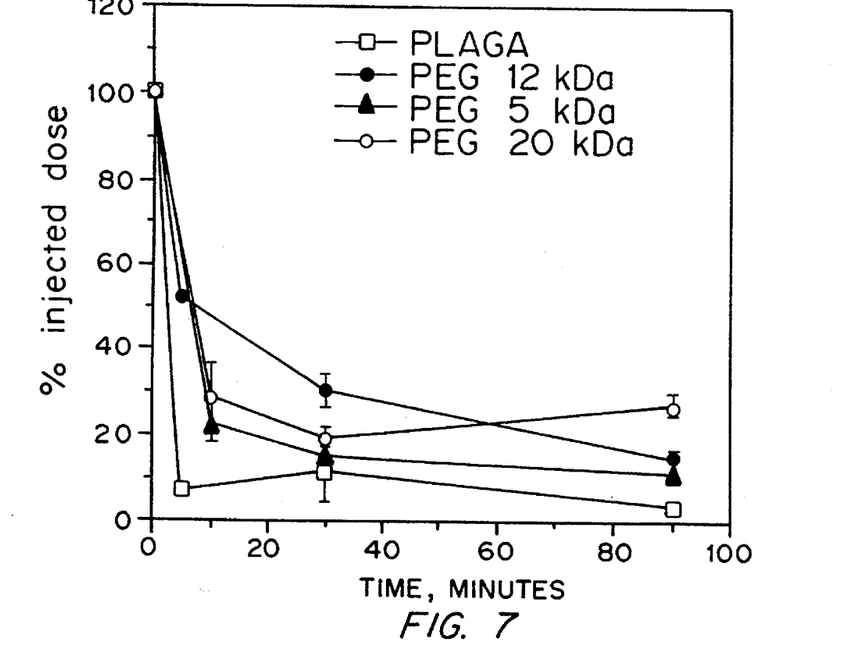
FIG. 7 is a graph of the clearance of PLGA and PEG-PLGA nanospheres in BALB-C mice as a function of percent of injected dosage in tissue versus time in minutes (open square, PLGA; closed square, PEG 12 kDa; closed triangle, PEG 5 kDa; and open circle, PEG, 20 kDa).
Figure 8:
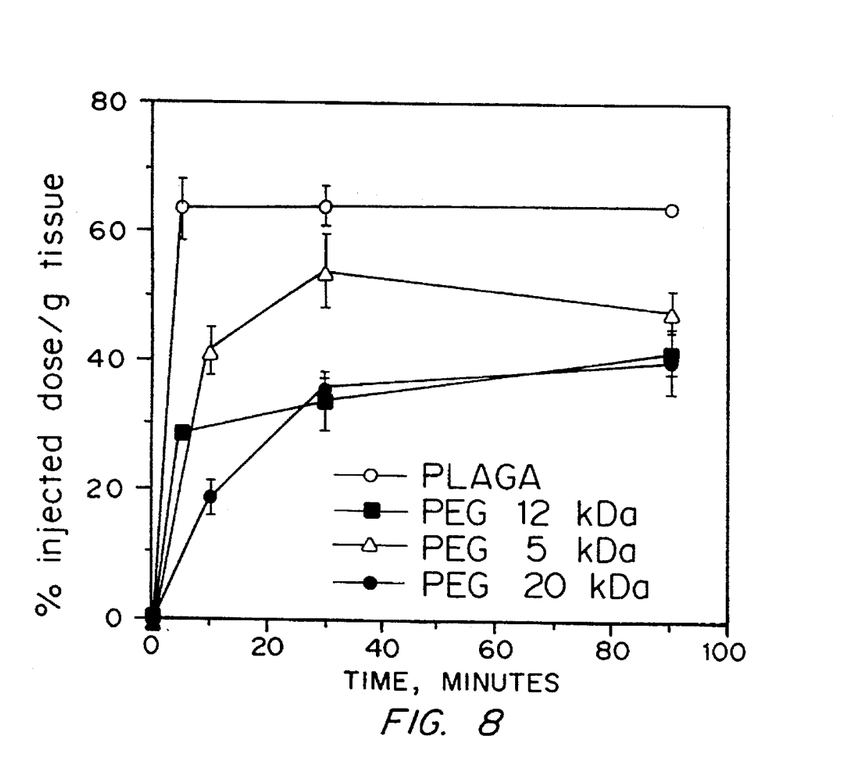
FIG. 8 is a graph of the accumulation in the liver of PLGA and PEG-PLGA nanospheres in BALB-C mice as a function of percent of injected dosage in tissue versus time in minutes (open square, PLGA; closed square, PEG 12 kDa; closed triangle, PEG 5 kDa; and open circle, PEG, 20 kDa).

In vivo results show that the higher the molecular weight (MW) of PEG, the longer the circulation time in the blood (the half-life) (See FIGS. 7 and 8).

Specific examples of poly(alkylene glycol) include poly(ethylene glycol), polypropylene 1,2-glycol poly(propylene oxide), and polypropylene 1,3-glycol. A preferred hydrophilic polymeric moiety is PEG of a molecular weight of appoximately 20,000 Da. Other hydrophilic polymers that can be used in place of poly(alkylene glycol) are polypyrrolidone, dextrans, and poly(vinyl alcohol) with a different percent acetyl content. A suitable commercial product is Pluronic F68 (BASF Corporation), a copolymer of polyoxyethylene and polyoxypropylene, which is approved by the U.S. Food and Drug Administration (FDA).

A polymer should be selected for the internal hydrophobic block or blocks of the copolymer that is biodegradable, biocompatible, and that has a terminal group that can react with the terminal hydroxyl group of the poly(alkylene glycol) to form a covalent linkage. It has been reported that the block copolymer of polylactic acid and poly(ethylene glycol) can be used for the injectable controlled administration of biologically active materials. However, it has now been discovered that the copolymer of lactic acid and glycolic acid, as well as other polymers such as polyanhydrides, polyhydroxybutyric acid, polyorthoesters other than the homopolymer of lactic acid, polysiloxanes, polycaprolactone, or copolymers prepared from the monomers of these polymers can also be used to prepare injectable nanoparticles for the delivery of biologically active materials. The variety of materials that can be used to prepare the injectable particles significantly increases the diversity of release rate and profile of release that can be accomplished in vivo.

Biodegradable polyanhydrides are disclosed in, for example, U.S. Pat. Nos. 4,757,128, 4,857,311, 4,888,176, and 4,789,724. Polyhydroxybutyrates are disclosed in Agostini, S., "Synthesis and Characterization of PHB," Ph.D. thesis, Case Western University, U.S.A. (1971) and U.S. Pat. No. 3,044,942. The teachings of these publications is incorporated by reference herein.

In a preferred embodiment, polyesters of poly(lactic-coglycolic)acid (PLGA) form the core of the particles. These polymers are approved for parenteral administration by the FDA. Because PLGA degrades via hydrolysis, in vivo degradation rates can be predicted from in vitro data. PLGA degrades to lactic and glycolic acids, substances found naturally in the body. Furthermore, by manipulating the molar ratio of lactic and glycolic acid and the molecular weight of the copolymers, different degradation patterns can be obtained.

The molecular weight of the polymer used to fabricate the nanoparticle and the chemical composition and stereochemical configuration of the polymer will affect the solubility of the polymer in various organic solvents as well as the crystallinity of the polymer. In this regard, a copolymer between lactic acid and glycolic acid is preferable.

To be ensure elimination from the body, the non-degradable PEG should have a molecular weight of approximately 20,000 Daltons or less. Several diblock copolymers of PEG-PLGA have been evaluated in which the molecular weight of PEG ranged from 350 to 20,000 Da, and the molecular weight of PLGA ranged from 350 to 200,000 Da. It was determined that the molecular weight of the hydrophilic and hydrophobic regions of the injectable particle affect the water solublity of the particles and thus their stability in aqueous solutions. As an example, PEG:PLGA 1:1 (weight ratio), (molecular weight PEG=molecular weight PLGA=5,000 Daltons) is freely soluble in water and can be used to form micelles of a mean diameter of about 20 nm as determined by using QUELS (quai elastic light scattering). To form larger nanoparticles with a dense core, this polymer should be blended with a hydrophobic polymer, such as PLGA.

The solubility in water or phosphate buffer solution (pH 7.4) decreases as the MW of PLGA increases from 5,000 to 20,000 Da. With PLGA-PEG (20,000–5,000 Da) stable nanospheres of a mean diameter of 120 to 140 nm were obtained using a simple emulsion technique. PLGA copolymers are preferred as the second polymer in the particle because it is soluble in ethyl acetate and acetone. Ethyl acetate or acetone is preferred over dichloromethane and chloroform because they are less toxic for in vivo applications.

Poly L-lactide is a polymer with a high degree of crystallinity. Poly D,L-lactide is less crystalline and more soluble in organic solvents. A random copolymer of D,L-lactide and glycolide in the ratio of 75:25 is very soluble in organic solvents, in particular in ethyl acetate. This copolymer is completely amorphous, which renders it a useful polymer for the fabrication of nanospheres and microspheres for controlled release.

Poly-L-lactide has a degradation time in vitro of months to years. The long degradation time is due to its higher crystallinity which protects the polymer from water penetration. Since D,L-lactide is amorphous, its degradation time is typically one to a number of months. Poly-glycolide also has a crystalline structure and a degradation time of one to several months. D,L-PLGA is amorphous, with a degradation time in vitro of weeks to months. As the glycolic acid ratio is increased, the rate of degradation is enhanced. Lactic acid has bulky methyl groups on the alpha carbon (—O—CH(CH$_3$—CH—) which makes it difficult for water molecules to access, while glycolic acid has a proton on the alpha carbon (—O—CH$_2$—CO—), which allows easier access of water molecules to the ester bonds.

Preparation of Diblock Copolymers

The preparation of the diblock copolymer of any of these polymers with poly(alkylene glycol) (PAG), and preferably poly(ethylene glycol), can be accomplished in a number of ways. Methods include: (i) reacting the polymer with monomethoxy poly(alkylene glycol), such as monomethoxy PEG or PEG protected with another oxygen protecting group known to those of skill in the art (such that one terminal hydroxyl group is protected and the other is free to react with the polymer); or (ii) polymerizing the polymer onto monomethoxy or otherwise monoprotected PAG, such as monoprotected PEG. Several publications teach how to carry out the latter type of reaction. Multiblock polymers have been prepared by bulk copolymerization of D,L-lactide and PEG at 170°–200° C. (X. M. Deng, et al., *J. of Polymer Science:* Part C: Polymer Letters, 28, 411–416 (1990). Three and four arm star PEG-PLA copolymers have been made by polymerization of lactide onto star PEG at 160° C. in the presence of stannous octoate as initiator. K. J. Zhu, et al., *J. Polym. Sci.*, Polym. Lett. Ed., 24,331 (1986), "Preparation, characterization and properties of polylactide (PLA)-poly-(ethylene glycol) (PEG) copolymers: a potential drug carrier". Triblock copolymers of PLA-PEG-PLA have been synthesized by ring opening polymerization at 180°–190° C. from D,L-lactide in the presence of PEG containing two end hydroxyl groups using stannous octoate as catalyst, without the use of solvent. The polydispersity (ratio Mw to Mn) was in the range of 2 to 3.

In an alternative embodiment, the polymer or monomers can be reacted with a poly(alkylene glycol) that is terminated with an amino function (available from Shearwater Polymers, Inc.) to form an amide linkage, which is in general stronger than an ester linkage. The amide linkage may provide a longer period of retention of the poly(alkylene glycol) on the surface of the nanoparticle.

Triblock or other types of block copolymers terminated with poly(alkylene glycol), and in particular, poly(ethylene glycol), can be prepared using the reactions described above, using a branched or other suitable poly(alkylene glycol) and protecting the terminal groups that are not to be reacted. Shearwater Polymers, Inc., provides a wide variety of poly-(alkylene glycol) derivatives. Examples are the triblock PEG-PLGA-PEG and the polymer of the structure Linear triblock copolymers such as PEG-PLGA-PEG can be prepared by refluxing the lactide, glycolide and polyethyleneglycol in toluene in the presence of stannous octoate. The triblock copolymer can also be prepared by reacting CH$_3$—O(CH$_2$CH$_2$)$_n$—O—PLGA—OH with HO—PLGA.

In one embodiment, a multiblock copolymer is prepared by reacting the terminal group of the hydrophobic polymeric moiety such as PLA or PLGA with a suitable polycarboxylic acid monomer, including but not limited to 1,3,5-benzenetricarboxylic acid, butane- 1,1,4-tricarboxylic acid, tricarballylic acid (propane- 1,2,3-tricarboxylic acid), and butane-1,2,3,4-tetracarboxylic acid, wherein the carboxylic acid moieties not intended for reaction are protected by means known to those skilled in the art. The protecting groups are then removed, and the remaining carboxylic acid groups reacted with poly(alkylene glycol). In another alternative embodiment, a di, tri, or polyamine is similarly used as the branching agent.

EXAMPLES

The preparation of the diblock copolymers of PLGA-PEG and PLA-PEG are described in detail below. These polymers were prepared with PEG of various chain lengths, and with various chain lengths of PLGA. Given this detailed description, one of skill in the art will know how to produce a wide variety of block copolymers suitable for fabrication into injectable nanospheres.

Materials and Methods

Low toxicity stannous octoate was purchased from ICN. D,L-lactide was purchased from Aldrich Chemical Company, and glycolide from Polysciences, Inc. These compounds were recrystallized before use from ethyl acetate. High purity monomethoxy PEG (M-PEG) with molecular weight 5,000, 12,000 and 20,000 was purchased from Shearwater Polymers, Inc. The number average molecular weight of the polymer was determined with on a Perkin-Elmer GPC system with an LC-25 refractive index detector equipped with a mixed bed Phenogel column filled with 5 µm particles from Phenomenex. Chloroform was used as the eluent, with a flow rate of 0.9 ml/min. The molecular weights were determined relative to narrow molecular weight polystyrene and poly(ethylene glycol) standards from Polysciences.

Thermal transition data was collected with a Perkin-Elmer DSC-7 (Newton Center, Mass.). The sample weight ranged from 20 to 25 mg. Indium was used for temperature and enthalpy calibrations. Each sample was subjected to a heat-cool-heat cycle from −60° to 150° C. with a rate of 10° C./min. Wide angle x-ray diffraction spectra were obtained with a Rigaku Rotaflex Diffractometer from Rigaku Corporation (Danvers, Mass.) with S=0.05 using a Nickel filtered Cu Kα source. The data was analyzed on a Micro Vax II computer. The IR spectra were recorded on a Nicolet 500 spectrometer using a polymer powder melted on sodium chloride crystals to obtain thin films. 13C NMR studies were conducted on samples dissolved in deuterated chloroform with a Nicolet NT-360 spectrometer. Peak fitting was carried out with a VG data system.

Example 1

Preparation of PLGA-PEG by Linking PLGA and PEG

The diblock copolymer PLGA-PEG was formed by reacting the hydroxyl endgroup of monomethoxy-PEG (M-PEG) with the carboxylic endgroup of PLGA. PLGA (0.1 mmol) and M-PEG (1.2 mmol) were dissolved in a mixture 5:2 of methylene chloride and dimethyl formamide. Equivalents of 1.2 mmol of 1-ethyl-3-(3'-dimethylaminopropyl)carbodiimide (EDC) and DMAP were added. After 24 hours of reaction at room temperature, the polymer was precipitated with water to remove non-reacted PEG and coupling reagents. The solid product was collected by centrifugation and washed three times with water. As detected by GPC, approximately 10% of diblock copolymer was formed.

Example 2

Preparation of PLGA-PEG by Polymerization of Lactic Acid and Glycolic Acid onto PEG European Patent Application Nos. 0 520 888 A1 and 0 520 889 A1A disclose that PLA-PEG diblock copolymer can be prepared from PEG lactic acid at 114° C. using toluene as the solvent and stannous octoate as the catalyst. This method was employed to synthesize a series of diblock copolymers of PLGA-PEG, starting with PEG of various chain lengths and progressively increasing the chain length of PLGA by decreasing the initial amount of PEG in the reaction mixture.

All siliconized glassware was heated at 130° C. overnight and cooled under vacuum before use. Lactide (4 g) and glycolide (1 g) were recrystallized from dry ethyl acetate the day before the polymerization reaction and dried under vacuum overnight. The monomers were added to the polymerization flasks and allowed to dissolve in dry toluene (10 ml) under argon, together with various amounts of PEG (0.5 to 5 g). The mixture was heated to 114° C. and then stannous octoate (10 mg) dissolved in toluene was added to the mixture.

Figure 2:
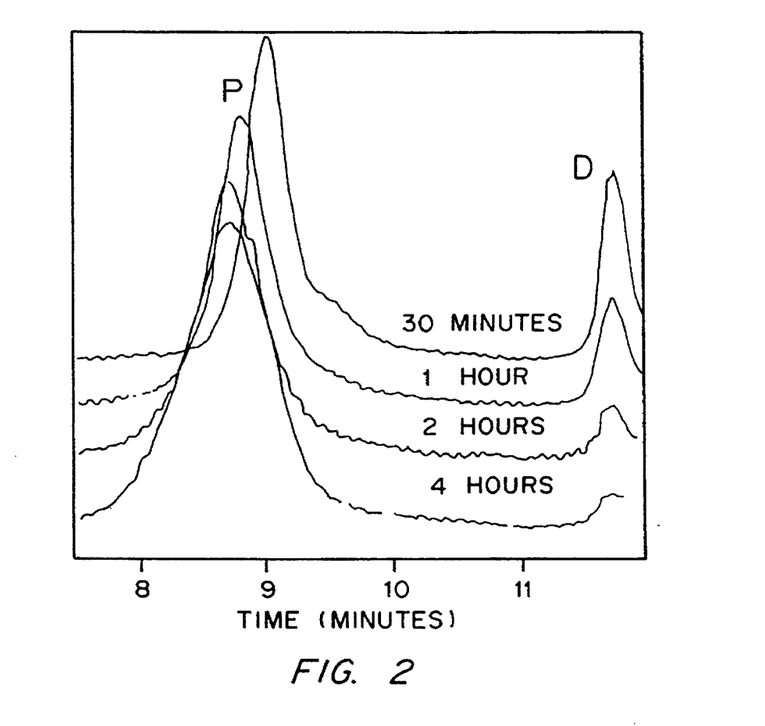
FIG. 2 is a gel permeation chromatogram of components in the polymerization reaction of lactide and glycolide in the presence of monomethoxy poly(ethylene glycol) after thirty minutes, one hour, two hours, and four hours. The consumption of lactide and glycolide into the polymer is represented by a decrease in peak D. The shift of peak P over time toward a lower retention time (higher molecular weight) indicates an addition reaction taking place on the hydroxyl end group of the poly(ethylene glycol) chain.

Samples were collected periodically and analyzed with GPC to determine the advancement of the reaction. FIG. 2 is a gel permeation chromatogram of components in the polymerization reaction of lactide and glycolide in the presence of monomethoxy poly(ethylene glycol) after thirty minutes, one hour, two hours, and four hours. The consumption of lactide and glycolide into the polymer is represented by a decrease in peak D. The shift of peak P over time toward a lower retention time (higher molecular weight) indicates an addition reaction occurring on the hydroxyl end group of the poly(ethylene glycol) chain.

It was determined that the higher the ratio of PEG in the reaction solution, the faster the reaction. For example, when PEG (MW 5000) is reacted with lactide and glycolide in a weight ratio of 50:50 PEG to monomers, the reaction is complete in less than twenty minutes. When PEG (MW 5000) is reacted with lactide and glycolide in a weight ratio of 10:90 PEG to monomers, the reaction is complete in approximately five hours.

After the starting materials were consumed, the reaction was stopped by cooling the reaction mixture to 0° C. and removing the toluene. The polymer product was redissolved in methylene chloride and purified by precipitation with hexane. After three reprecipitations, the polymer was washed with water.

Figure 3:
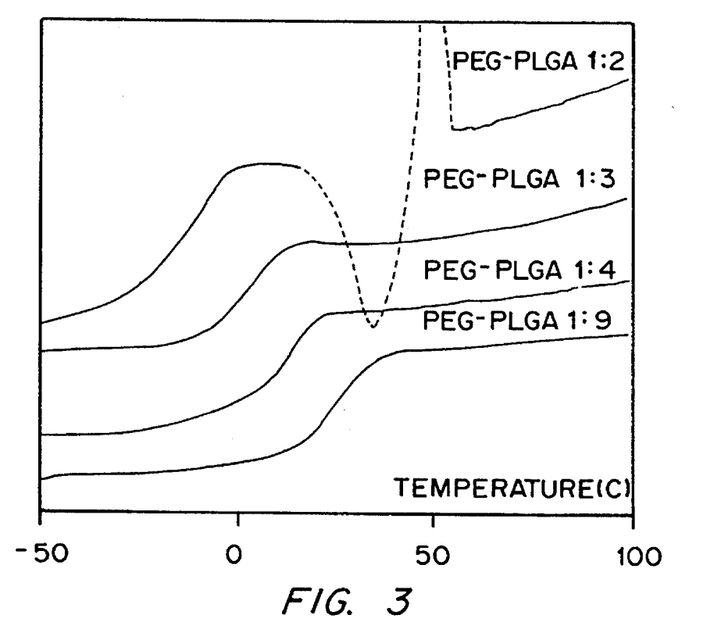
FIG. 3 is a thermogram of the exothermic heat flow (expressed in arbitrary units) as a function of temperature, for PEG-PLGA in weight ratios of 1:2, 1:3, 1:4, and 1:9, collected on a Perkin-Elmer Differential Scanning Calorimeter. The sample weight ranged from 20 to 25 mg. Indium was used for temperature and enthalpy calibrations. Each polymer sample was subjected to a heat-cool-heat cycle from $-60°$ to $150°$ C. with a rate of $10°$ C. per minute.

FIG. 3 is a graph of the change in temperature (°C.) for PEG-PLGA in weight ratios of 1:2, 1:3, 1:4, and 1:9, collected on a Perkin-Elmer Differential Scanning Calorimeter. The sample weight ranged from 20 to 25 mg. Indium was used for temperature and enthalpy calibrations. Each cycle was subjected to a heat-cool-heat cycle from −60° to 150° C. with a rate of 10° C. per minute. Random lactic acid-ethylene oxide copolymers show two distinct Tg's, suggesting a phase separation inside the polymer. The single Tg observed in this case may be due to an entanglement effect of long PEG and PLGA chains in the polymers, which cannot easily phase-separate.

Polymer characterization nuclear magnetic resonance confirmed that the product was pure diblock PEG-PLGA. The polymers were used to form the nanospheres for parenteral administration.

II. Preparation of Block Copolymers Terminated with a Biologically Active Material An injectable particle can be prepared that includes a substance to be delivered and a polymer that is covalently bound to a biologically active molecule, preferably an antibody or antibody fragment, wherein the particle is prepared in such a manner that the biologically active molecule is on the outside surface of the particle. Injectable particles with antibody or antibody fragments on their surfaces can be used to target specific cells or organs as desired for the selective dosing of drugs.

The biologically active molecule, and in particular, an antibody or antibody fragment, can be covalently bound to the block copolymer by reaction with the terminal hydroxyl group of the poly(alkylene glycol) by any method known to those skilled in the art. For example, the hydroxyl group can be reacted with a terminal carboxyl group or terminal amino group on the molecule or antibody or antibody fragment, to form an ester or amide linkage, respectively. Alternatively, the molecule can be linked to the poly(alkylene glycol) through a difunctional spacing group such as a diamine or a dicarboxylic acid, including but not limited to sebacic acid, adipic acid, isophthalic acid, terephthalic acid, fumaric acid, dodecanedicarboxylic acid, azeleic acid, pimelic acid, suberic acid (octanedioic acid), itaconic acid, biphenyl-4,4'-dicarboxylic acid, benzophenone-4,4'-dicarboxylic acid, and p-carboxyphenoxyalkanoic acid. In this embodiment, the spacing group is reacted with the hydroxyl group on the poly(alkylene glycol), and then reacted with the biologically active molecule. Alternatively, the spacing group can be reacted with the biologically active molecule or antibody or antibody fragment, and then reacted with the hydroxyl group on the poly(alkylene glycol). The reaction should by accomplished under conditions that will not adversely affect the biological activity of the molecule being covalently attached to the nanoparticle. For example, conditions should be avoided that cause the denaturation of proteins or peptides, such as high temperature, certain organic solvents and high ionic strength solutions, when binding a protein to the particle. For example, organic solvents can be eliminated from the reaction system and a water-soluble coupling reagent such as EDC used instead.

Example 3

Preparation of Block Copolymer Terminated with an Antibody

The terminal —COOH group in PLGA is activated with N-hydroxysuccinimide ester using EDC and N-hydroxysccinimide in $CH_2Cl_2$. After isolation of the activated material, antibody in water is added to the solution of PLGA-hydroxysuccinimide ester in aqueous DMF, CH3CH, or DMSO solution. After 24 hours, the reaction mixture is applied onto HPLC (ion-exchange, gel-filtration, or reversed-phase) and the desired conjugate fractioned.

III. Substances to be Delivered

A wide range of biologically active materials or drugs can be incorporated into the polymer at the time of nanoparticle formation. The substances to be incorporated should not chemically interact with the polymer during fabrication, or during the release process. Additives such as inorganic salts, BSA (bovine serum albumin), and inert organic compounds can be used to alter the profile of substance release, as known to those skilled in the art. Biologically-labile materials, for example, procaryotic or eucaryotic cells, such as bacteria, yeast, or mammalian cells, including human cells, or components thereof, such as cell walls, or conjugates of cellular can also be included in the particle. The term biologically active material refers to a peptide, protein, carbohydrate, nucleic acid, lipid, polysacccaride or combinations thereof, or synthetic inorganic or organic molecule, that causes a biological effect when administered in vivo to an animal, including but not limited to birds and mammals, including humans. Nonlimiting examples are antigens, enzymes, hormones, receptors, and peptides. Examples of other molecules that can be incorporated include nucleosides, nucleotides, antisense, vitamins, minerals, and steroids.

Injectable particles prepared according to this process can be used to deliver drugs such as nonsteroidal anti-inflammatory compounds, anesthetics, chemotherapeutic agents, immunotoxins, imunosuppressive agents, steroids, antibiotics, antivirals, antifungals, and steroidal antiinflammatories, anticoagulants. For example, hydrophobic drugs such as lidocaine or tetracaine can be entrapped into the injectable particles and are released over several hours. Loadings in the nanoparticles as high as 40% (by weight) have been achieved. Hydrophobic materials are more difficult to encapsulate, and in general, the loading efficiency is decreased over that of a hydrophilic material.

In one embodiment, an antigen is incorporated into the nanoparticle. The term antigen includes any chemical structure that stimulates the formation of antibody or elicits a cell-mediated humoral response, including but not limited to protein, polysaccharide, nucleoprotein, lipoprotein, synthetic polypeptide, or a small molecule (hapten) linked to a protein carrier. The antigen can be administered together with an adjuvant as desired. Examples of suitable adjuvants include synthetic glycopeptide, muramyl dipeptide. Other adjuvants include killed *Bordetella pertussis,* the liposaccaride of Gram-negative bacteria, and large polymeric anions such as dextran sulfate. A polymer, such as a polyelectrolyte, can also be selected for fabrication of the nanoparticle that provides adjuvant activity.

Specific antigens that can be loaded into the nanoparticles described herein include, but are not limited to, attenuated or killed viruses, toxoids, polysaccharides, cell wall and surface or coat proteins of viruses and bacteria. These can also be used in combination with conjugates, adjuvants, or other antigens. For example, *Haemophilius influenzae* in the form of purified capsular polysaccharide (Hib) can be used alone or as a conjugate with diptheria toxoid. Examples of organisms from which these antigens are derived include poliovirus, rotavirus, hepatitis A, B, and C, influenza, rabies, HIV, measles, mumps, rubella, *Bordetella pertussus, Streptococcus pneumoniae, C. diptheria, C. tetani,* Cholera, Salmonella, Neisseria, and Shigella.

Non-pharmaceutical uses for the injectable particles include delivery of food additives, including stabilizers and dispersants or other viscosity modifying agents, controlled and selective delivery of pesticides, herbicides, insecticides, fertilizer, and pheromones, and in color and ink formulations in the printing and ink industry.

Polymers loaded as described herein can also be used to coat implantable devices, i.e., stents, catheters, artificial vascular grafts, and pacemakers. The device can be coated with the lyophilized powder of the injectable particles, or otherwise as known to those skilled in the art. The coating can release antibiotics, anti-inflammatories, or anti-clotting agents at a predetermined rate, to prevent complications related to the implanted devices. Controlled delivery devices prepared as described herein can also be used as ocular inserts for extended release of drugs to the eye.

IV. Preparation and Characterization of Nanoparticles

Injectable particles are prepared by mixing the substance to be encapsulated with the block copolymer and precipitating the mixture from a solvent system in such a manner that the hydrophobic moieties of the copolymer are in the core of the particle and the hydrophilic poly(alkylene glycol) moieties are on the surface of the particle.

For example, the mixture of block copolymer and substance to be delivered can be mixed in a common solvent such as ethyl acetate or methylene chloride. An organic solvent should be selected that is a nonsolvent for the poly(alkylene glycol) homopolymer, and a solvent for the homopolymer of the other unit or units of the block copolymer. An emulsion is formed by adding distilled deionized water to the solution. Slow evaporation of the organic solvent allows a reorganization of the polymer chains inside and on the surface of the droplets. The poly(alkylene glycol), which is not soluble in organic solvent, tends to migrate to the aqueous phase, while, the other unit of the copolymer, which is not soluble in water, remains inside the droplets and forms the core of the nanospheres after the completion of solvent evaporation. PEG chains inside the core should be avoided, because this can lead to absorption of water by the core followed by the accelerated and uncontrolled release of the drugs.

After removal of the organic solvent, the injectable particles are isolated from the aqueous phase by centrifugation. They can later be readily redispersed in water.

In an alternative embodiment, acetone, methanol, or ethanol and their aqueous solutions can be used in place of the distilled deionized water. In general, water is preferred because it forces a higher concentration of poly(alkylene glycol) to the surface of the particle. However, acetone can be used as the precipitating solvent of the copolymer or second polymer, such as polyanhydride, is sensitive to water. In an alternative embodiment, the block copolymer is blended with a second polymer, for example PLGA-PEG mixed with PLGA or PLA, prior to fabrication into the injectable particles, to provide different properties on the injectable particles, for example, altering their half-life in vivo. Addition of PLGA PEG to other polymers increases in vivo half-life.

In a typical embodiment, the second polymer is mixed with the block copolymer in a ratio of greater than 0 up to 100.

The substance to be delivered is mixed with the copolymer or copolymer blend in a ratio of greater than 0 to 99, and more preferably, in a ratio of 1 to 70.

Light scattering studies have indicated that the size of the resulting particles is determined by the viscosity of the organic phase, ratio of organic to aqueous phase, and sonication power and time: increased viscosity yields bigger particles and higher ratio of aqueous phase volume as compared to organic phases yields smaller particles. A example of the effect of the sonication power and time is as follows: 25 mg polymer/2 ml $CH_2C_{12}$ is added to 30 ml of 0.3% polyvinyl alchol solution. The mixture is vortexed for 30 seconds at the maximum strength and then sonicated by probe sonicator for 30 seconds at the output 7. The conditions reproducibly yield 15 nm particles. These parameters can be optimized to obtain nanospheres of a mean size of about 150 nm with a narrow unimodal size distribution.

Methods for the preparation and characterization of injectable nanoparticles are described in detail below, using PLGA-PEG and PLA-PEG as the block copolymers, and PLGA as the blending polymer, for purposes of illustration. As described, however, the invention is not limited to these specific embodiments.

Example 4

Preparation of Nanospheres of PLGA-PEG

Sterically stabilized particles were prepared from diblock PLGA-PEG copolymers or from blends of PLGA and PLGA-PEG. These polymers were dissolved in a common solvent (ethyl acetate or methylene chloride). An oil-in-water emulsion was formed by vortexing and sonicating the mixture for 30 seconds. The organic solvent was then slowly evaporated, at room temperature, by gentle stirring for two hours. Slow removal of the solvent allowed reorganization of the polymer chains inside and on the surface of the droplets, wherein the more hydrophilic PEG chains migrated to the water interface, and the more hydrophobic PLGA chains remained inside the droplets to form the core of the nanospheres.

After removal of the organic solvent, the nanospheres were isolated from the aqueous phase by centrifugation. The nanospheres could later be readily redispersed in water.

Figure 4:
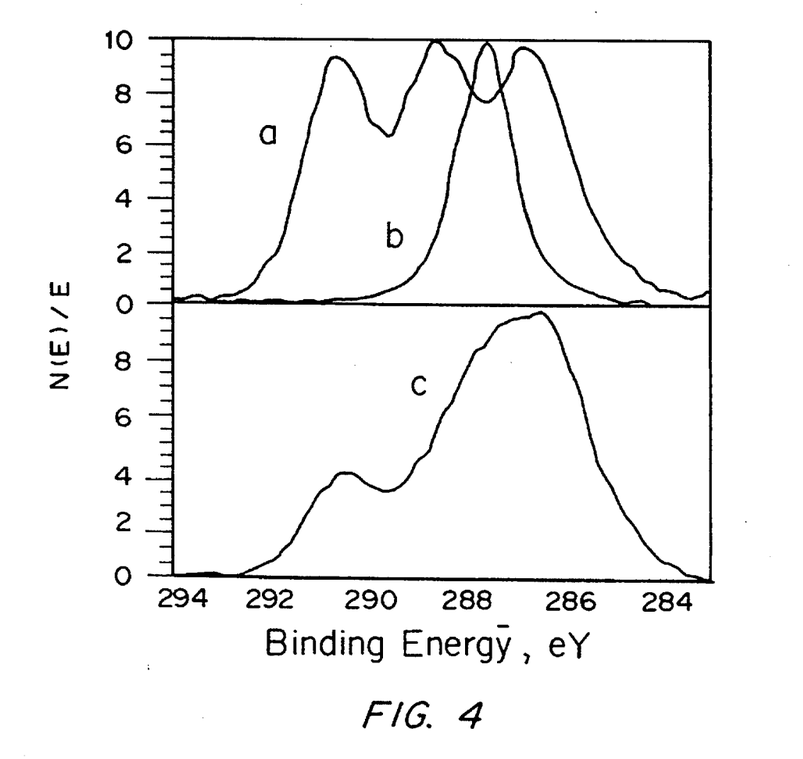
FIG. 4 is an X-ray photoelectron spectrum of the surface composition of lyophilized particles of PLGA-PEG using MgK$\alpha$ X-rays at a power of 300 W.

To verify that PEG was present on the surface of the nanospheres, the surface composition of lyophilized particles was determined by X-ray photoelectron spectroscopy (XPS). FIG. 4 is an X-ray photoelectron spectrum of the surface composition of lyophilized particles of PLGA-PEG using MgK-α X-rays with a power of 300 W. Carbon 1s envelopes were observed on analysis of the nanosphere powder. One predominant carbon environment is observed for PEG, corresponding to the ether carbon $\underline{C}$—O. The spectrum of the PLGA polymer exhibits three predominant carbon environments. All of these peaks are evident in the XPS spectrum of PEG-PLGA nanospheres, however, the PEG peak is predominant. Since the information obtained from XPS corresponds to the surface layers of the nanosphere (about 5 nm deep), the spectrum indicates that PEG is concentrated on the surface of the nanosphere powder.

Moreover, it was confirmed that PEG remains on the surface of the nanoparticle after incubation in distilled water for 24 hours. The nanospheres were recovered by centrifugation and freeze-drying. The XPS analysis shows that over time, the PEG peak diminished relative to the peaks corresponding to the PLGA, meaning that PEG was partially, but not entirely, removed.

Figure 5:
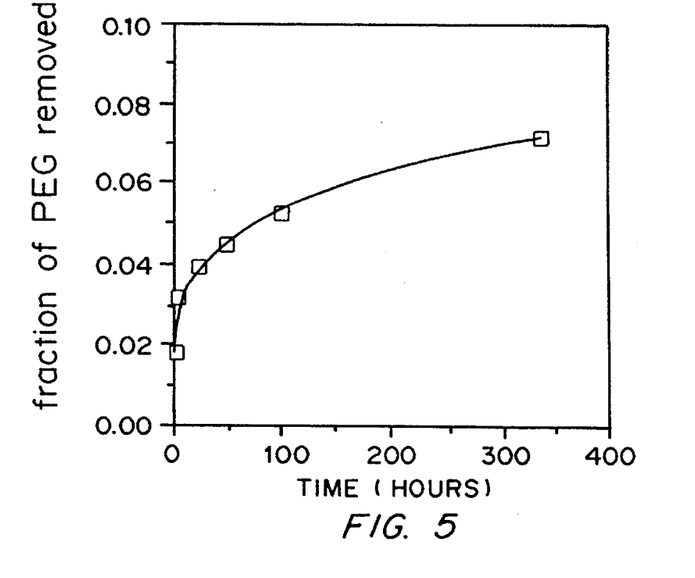
FIG. 5 is a graph of the fraction of poly(ethylene glycol) removed from the surface of the nanospheres during incubation at $37°$ C. in phosphate buffer.

FIG. 5 is a graph of the fraction of poly(ethylene glycol) removed from the surface of the nanospheres during incubation for 24 hours at 37° C. in phosphate buffer. This in vitro data supports the observation from XPS that less than 4% of the total PEG content is removed from the surface of the nanosphere under these conditions.

Example 5

Preparation of PLA-PEG Nanospheres Containing an Active Component

A solution of 2 ml methylene chloride, 25 mg lidocaine and 25 mg diblock polymers of Example 2 was prepared. After removal of methylene chloride by stirring the solution, nanospheres were isolated by centrifugation, giving lidocaine-loaded particles of a diameter of 15 nm.

V. Evaluation of Biodistribution of $^{111}$In-labeled Nanoparticles in vivo

Nanospheres prepared as described herein can be labelled with Indium 111, which has been used for gamma-scintigraphy studies in humans. Its short half-life (six hours) reduces the problems of disposal and contamination. Indium 111 also has lower energy radiation compared to other labels. These properties render it an attractive compound for labelling nanospheres for in vivo studies.

The radioactive label can be attached to the surface of the already prepared nanospheres by first chelating In and diethyltriamiopentaacctic acid (DTPA) by mixing both compounds in aqueous ethanol, then reacting primary amino groups in this chelate with carboxy groups on the particle' surface (ester group in PLGA on the surface should partially hydolyzed to produce free carboxylic acids) by EDC to provide surface-labeled particles. Alternatively, the label is incorporated into the core during fabrication. The release of the label should be slow enough that sufficient radioactivity will be retained in the device for evaluation of the in vivo organ distribution by gamma-scintigraphy.

Example 6

Evaluation of Biodistribution of $^{111}$In-labeled Nanoparticles in vivo

Indium 111 was directly attached to the PLGA and PEG polymer chains by complex formation. In and diethyltriamiopentaacetic acid (DTPA) are reacted with stearylamine. The resulting compound, In-DTPA-stearylamide, is hydrophobic enough to interact to the PLGA core. In this case, Mws of PLGA and PEG has little effect on the interaction. After incubation at 37° C. in PBS or horse serum for more than 24 hours, there was no label loss, as assessed by measuring the radioactivity of the supernatant solutions after centrifugation. This labelling method is therefore useful for in vivo studies, by gamma-scintigraphy or by direct measurement of the radioactivity in the blood and/or different organs.

Preliminary biodistribution experiments were performed by injecting $^{111}$In-labeled uncoated PLGA nanospheres and PEG-coated PLGA nanospheres into the tail vein of BALB/C mice (18–20 g). Five minutes after injection of uncoated PLGA nanospheres, 40% of nanosphere-associated $^{111}$In radioactivity was found in the liver and approximately 15% in the blood. In the case of PEG-coated nanospheres, the results were reversed: 15% of injected radioactivity in the liver, 60% in the blood. After four hours, 30% of the nanospheres were still circulating in the blood, whereas the non-coated ones had disappeared completely from the blood.

Figure 6:
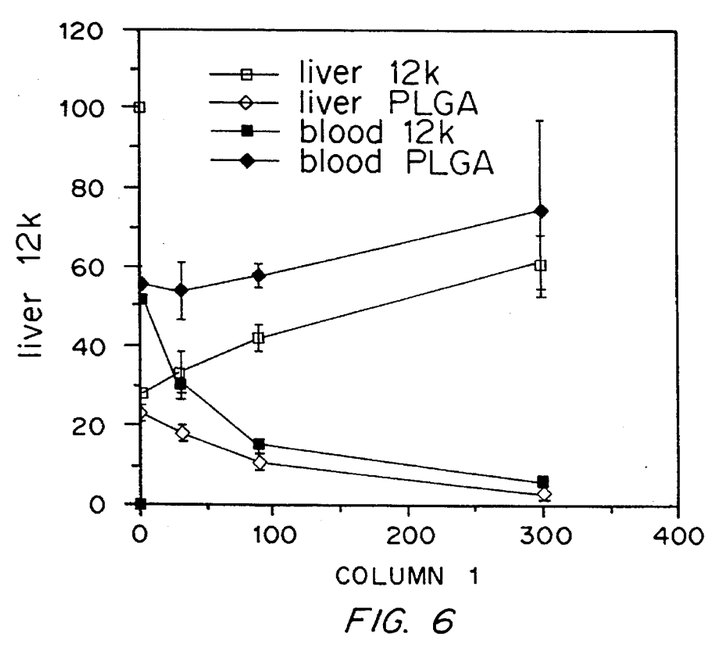
FIG. 6 is an graph of the biodistribution of PLGA and PEG-PLGA in the liver and blood as a function of percent of injected dosage over time in minutes (open square, 12 kDa PEG-PLGA in liver; closed diamond, uncoated PLGA in the liver; closed square, 12 kDa PEG-PLGA in blood; and open diamond, uncoated PLGA in the blood).

FIG. 6 is a graph of the biodistribution of PLGA and PEG-PLGA in the liver and blood as a function of percent of injected dosage over time in minutes (open square, PEG-PLGA with 12 kDa PEG in liver; closed diamond, uncoated PLGA in the liver; closed square, 12 k Da PEG-PLGA in blood; and open diamond, uncoated PLGA in the blood). As indicated, the PEG-coated PLGA nanospheres remained in the blood for an extended period, while the uncoated PLGA nanospheres concentrated in the liver, where the are degraded and cleared.

FIG. 7 is a graph of the clearance of uncoated PLGA and PEG-PLGA nanospheres in BALB-C mice as a function of percent of injected dosage in tissue versus time in minutes (open square, PLGA; closed square, PLGA-PEG with 12 k Da PEG; closed triangle, PLGA-PEG with 5 k Da PEG; and open circle, PLGA-PEG, with 20 k Da PEG). As indicated, the uncoated nanospheres were quickly cleared, and in general, the higher the molecular weight of the PEG, the longer the circulation time.

FIG. 8 is a graph of the accumulation in the liver of uncoated PLGA and PEG-PLGA nanospheres in BALB-C mice as a function of percent of injected dosage in tissue versus time in minutes (open square, PLGA; closed square, PEG-PLGA with 12 k Da PEG; closed triangle, PLGA-PEG with 5 kDa PEG; and open circle, PLGA-PEG with 20 kDa PEG). The uncoated PLGA nanospheres more quickly accumulated in the liver than the non-coated particles.

VI. Pharmaceutical Administration of Nanospheres

The injectable particles described herein can be administered to a patient in a variety of routes, for example, orally, parenterally, intravenously, intradermally, subcutaneously, or topically, in liquid, cream, gel or solid form.

The particles can be lyophilized and then formulated into an aqueous suspension in a range of microgram/ml to 100 mg/ml prior to use. Alternatively, the particles can be formulated into a paste, ointment, cream, or gel, or transdermal patch.

The nanoparticle should contain the substance to be delivered in an amount sufficient to deliver to a patient a therapeutically effective amount of compound, without causing serious toxic effects in the patient treated. The desired concentration of active compound in the nanoparticle will depend on absorption, inactivation, and excretion rates of the drug as well as the delivery rate of the compound from the nanoparticle. It is to be noted that dosage values will also vary with the severity of the condition to be alleviated. It is to be further understood that for any particular subject, specific dosage regimens should be adjusted over time according to the individual need and the professional judgment of the person administering or supervising the administration of the compositions.

The particles can be administered once, or may be divided into a number of smaller doses to be administered at varying intervals of time, depending on the release rate of the particle, and the desired dosage.

This invention has been described with reference to its preferred embodiments. Variations and modifications of the invention will be obvious to those skilled in the art from the foregoing detailed description of the invention. It is intended that all of these variations and modifications be included within the scope of the appended claims.

We claim:

1. A microparticle or nanoparticle comprising an imaging agent and a copolymer consisting essentially of poly(alkylene glycol) and a polymer selected from the group consisting of polyanhydride, polyhydroxybutyric acid, polyorthoesters, polysiloxanes, polycaprolactone, poly(lactic acid), poly(glycolic acid), poly(lactic-co-glycolic acid) and copolymers prepared from the monomers of these polymers, wherein an effective amount of the poly(alkylene glycol) is on the surface of the particles to decrease uptake by the reticuloendothelial system.

2. The nanoparticles or microparticles of claim 1 comprising molecules covalently bound to the surface of the particle via the terminal hydroxyl group of the poly(alkylene glycol), wherein the molecules are selected from the group consisting of molecules to be delivered to a site which have biological activity, molecules which can be detected, targeting molecules, and molecules affecting the charge, lipophilicity or hydrophilicity of the nanoparticles or microparticles.

3. The nanoparticles or microparticles of claim 2, wherein the targeting molecule is selected from the group consisting of compounds specifically reactive with a cell surface component.

4. The nanoparticles or microparticles of claim 3 wherein the molecule is selected from the group consisting of antibodies and antibody fragments.

5. The nanoparticles or microparticles of claim 3, wherein the poly(alkylene glycol) is covalently bound to the targeting molecules.

6. The nanoparticles or microparticles of claim 1 wherein the diameter is less than one micron.

7. The nanoparticles or microparticles of claim 1 wherein the diameter between one and 1000 microns.

8. The nanoparticles or microparticles of claim 1 wherein the imaging agent is selected from the group of agents detectable by x-ray, fluorescence, magnetic resonance imaging, radioactivity, ultrasound, CT and PET.

9. The nanoparticles or microparticles of claim 1, wherein the poly(alkylene glycol) is poly(ethylene glycol).

10. The nanoparticles or microparticles of claim 1 wherein the copolymer is a copolymer of a polymer selected from the group consisting of poly(lactic-co-glycolic acid), poly(lactic acid), and poly(glycolic acid), the copolymer having two or more moieties of poly(alkylene glycol).

11. The nanoparticles or microparticles of claim 1 wherein the copolymer is a copolymer of a polymer selected from the group consisting of poly(lactic-co-glycolic acid), poly(lactic acid), and poly(glycolic acid) with poly(alkylene glycol), blended with poly(lactic-co-glycolic acid).

12. The nanoparticles or microparticles of claim 1 wherein the surface of the nanoparticles or microparticles is modified by attaching biodegradable polymers of the same structure as those forming the core of the injectable particles.

13. A method for making nanoparticles or microparticle comprising combining together imaging agent and a copolymer consisting essentially of poly(alkylene glycol) and a polymer selected from the group consisting of polyanhydride, polyhydroxybutyric acid, polyorthoesters other than the homopolymer of lactic acid, polysiloxanes, polycaprolactone, poly(lactic acid), poly(glycolic acid), poly(lactic-co-glycolic acid) and copolymers prepared from the monomers of these polymers, and forming nanoparticles or microparticles, wherein an effective amount of the poly(alkylene glycol) is on the surface of the particles to decrease uptake by the reticuloendothelial system.

14. The method of claim 13 wherein the imaging agent is detectable by ultrasound.

15. The method of claim 13 further comprising covalently binding to the surface of the nanoparticles or microparticles via the terminal hydroxyl group of the poly(alkylene glycol) molecules selected from the group consisting of molecules which have biological activity, molecules which can be detected, targeting molecules, and molecules affecting the charge, lipophilicity or hydrophilicity of the particle.

16. The method of claim 15 further comprising targeting the nanoparticles or microparticles for delivery to a specific cell type by attaching to the surface of the particle a targeting molecule selected from the group consisting of compounds specifically reactive with a cell surface component.

17. The method of claim 13 wherein the imaging agent is selected from the group of imaging agents detectable by x-ray, fluorescence, magnetic resonance imaging and radioactivity.

18. The method of claim 13 wherein the copolymer is a copolymer of a polymer selected from the group consisting of poly(lactic-co-glycolic acid), poly(lactic acid), and poly(glycolic acid), the copolymer having two or more moieties of poly(alkylene glycol).

19. The method of claim 13 wherein the copolymer is a copolymer of a polymer selected from the group consisting of poly(lactic-co-glycolic acid), poly(lactic acid), and poly(glycolic acid) with poly(alkylene glycol), blended with poly(lactic-co-glycolic acid).

20. The method of claim 13 wherein the surface of the nanoparticles or microparticles is modified by attaching biodegradable polymers of the same structure as those forming the core of the injectable particles.

21. A method for imaging a region in a patient comprising administering to the patient nanoparticles or microparticles comprising an imaging agent and a copolymer consisting essentially of poly(alkylene glycol) and a polymer selected from the group consisting of polyanhydride, polyhydroxybutyric acid, polyorthoesters, polysiloxanes, polycaprolactone, poly(lactic acid), poly(glycolic acid), poly(lactic-co-glycolic acid) and copolymers prepared from the monomers of these polymers, wherein an effective amount of the poly(alkylene glycol) is on the surface of the particles to decrease uptake by the reticuloendothelial system.

22. The method of claim 21 wherein the imaging agent is selected from the group of agents detectable by x-ray, fluorescence, magnetic resonance imaging, radioactivity, ultrasound, PET, and CT.

23. The method of claim 22 wherein the imaging agent is a gas selected from the group consisting of air, oxygen and perfluorocarbon.

24. The nanoparticles or microparticles of claim 8 wherein the imaging agent is a gas present in an effective amount to be detected by ultrasound.

25. The nanoparticles or microparticles of claim 24 wherein the gas is selected from the group consisting of air, oxygen and perfluorocarbon.

26. The nanoparticles or microparticles of claim 25 wherein the gas is perfluorocarbon.

27. The method of claim 17 wherein the imaging agent is a gas present in an effective amount to be detected by ultrasound.

28. The method of claim 27 wherein the gas is selected from the group consisting of air, oxygen and perfluorocarbon.

29. The method of claim 28 wherein the gas is perfluorocarbon.

30. The method of claim 23 wherein the gas is perfluorocarbon.

* * * * *